United States Patent [19]

Syverson

[11] Patent Number: 5,618,554
[45] Date of Patent: Apr. 8, 1997

[54] INHIBITION OF EXOPROTEIN USING AMINE COMPOSITIONS IN ABSORBENT ARTICLE AND METHOD THEREOF

[75] Inventor: Rae E. Syverson, Fond du Lac, Wis.

[73] Assignee: Kimberly-Clark Corporation, Neenah, Wis.

[21] Appl. No.: 487,875

[22] Filed: Jun. 7, 1995

[51] Int. Cl.$^6$ ............................................. A61F 13/20
[52] U.S. Cl. ...................... 424/431; 424/402; 424/404; 424/434
[58] Field of Search ................... 424/402, 404, 424/431, 434

[56] References Cited

U.S. PATENT DOCUMENTS

| | | | |
|---|---|---|---|
| 2,154,449 | 4/1939 | Hoffman et al. | 99/90 |
| 2,190,714 | 2/1940 | Hoffman et al. | 99/224 |
| 2,290,173 | 8/1940 | Epstein et al. | 167/22 |
| 2,290,174 | 10/1940 | Epstein et al. | 167/22 |
| 2,321,594 | 6/1943 | Harris | 260/404 |
| 2,340,311 | 2/1944 | Donovan | 128/285 |
| 2,440,141 | 4/1948 | Donovan | 128/285 |
| 2,466,663 | 4/1949 | Russ et al. | 167/58 |
| 2,467,884 | 4/1949 | Elias | 167/58 |
| 2,623,841 | 12/1952 | Taub | 167/58 |
| 2,854,978 | 10/1958 | Millman et al. | 128/285 |
| 3,091,241 | 5/1963 | Kellett | 128/270 |
| 3,172,817 | 3/1965 | Leupold et al. | 167/90 |
| 3,331,742 | 7/1967 | Babayan | 167/82 |
| 3,490,454 | 1/1970 | Goldfarb et al. | 128/285 |
| 3,629,454 | 12/1971 | Barr et al. | 424/320 |
| 3,639,561 | 2/1972 | Gordon et al. | 424/28 |
| 3,652,764 | 3/1972 | Lamberti et al. | 424/235 |
| 3,994,298 | 11/1976 | Des Marais | 128/285 |
| 4,002,775 | 1/1977 | Kabara | 426/532 |
| 4,046,914 | 9/1977 | Hallgren et al. | 424/312 |
| 4,067,961 | 1/1978 | Laughlin | 424/15 |
| 4,273,118 | 6/1981 | Smith | 128/156 |
| 4,286,596 | 9/1981 | Rubinstein | 128/270 |
| 4,289,824 | 9/1981 | Smith | 428/288 |
| 4,300,561 | 11/1981 | Kaczmarzyk et al. | 128/285 |
| 4,343,788 | 8/1982 | Mustacich et al. | 424/78 |
| 4,343,798 | 8/1982 | Fawzi | 424/240 |
| 4,377,167 | 3/1983 | Kaczmarzyk et al. | 128/285 |
| 4,385,632 | 5/1983 | Odelhog | 604/360 |
| 4,392,848 | 7/1983 | Lucas et al. | 604/53 |
| 4,405,323 | 9/1983 | Auerbach | 604/285 |
| 4,406,884 | 9/1983 | Fawzi et al. | 424/81 |
| 4,410,442 | 10/1983 | Lucas et al. | 252/107 |
| 4,430,381 | 2/1984 | Harvey et al. | 428/284 |
| 4,431,427 | 2/1984 | Lefren et al. | 604/285 |
| 4,479,795 | 10/1984 | Mustacich et al. | 604/53 |
| 4,489,097 | 12/1984 | Stone | 424/318 |
| 4,585,792 | 4/1986 | Jacob et al. | 514/474 |
| 4,661,101 | 4/1987 | Sustmann | 604/360 |
| 4,675,014 | 6/1987 | Sustmann et al. | 604/375 |
| 4,722,937 | 2/1988 | Jacob et al. | 514/474 |
| 4,752,617 | 6/1988 | Kern | 514/547 |
| 4,959,341 | 9/1990 | Wallach | 502/404 |
| 5,068,064 | 11/1991 | Proietto et al. | 260/404.5 |
| 5,080,902 | 1/1992 | Allenmark et al. | 424/430 |
| 5,201,326 | 4/1993 | Kubicki et al. | 128/832 |
| 5,208,257 | 5/1993 | Kabara | 514/552 |

FOREIGN PATENT DOCUMENTS

| | | |
|---|---|---|
| 1123155 | 5/1982 | Canada. |
| 0395099A2 | 10/1990 | European Pat. Off.. |
| 0405993A3 | 1/1991 | European Pat. Off.. |
| 0483812A1 | 5/1992 | European Pat. Off.. |
| 0483835A1 | 5/1992 | European Pat. Off.. |
| 0510619A1 | 11/1992 | European Pat. Off.. |
| 1307930 | 9/1962 | France. |
| 3309530C1 | 10/1984 | Germany. |
| 63-309604 | 12/1988 | Japan. |

OTHER PUBLICATIONS

Article Entitled "A Rapid, Sensitive Method For Detection Of Alkaline Phosphatase–Conjugated Anti–Antibody Of Western Blots" authored by Blake, Johnston, Russell–Jones and Gotschlich Analytical Biochemistry 136, 175–179 (1984).

Aritcle Entitled "Effect of Glycerol Monolaurate on Bacterial Growth and Toxin Production" authored by Schlievert, Deringer, Kim, Projan and Novick, Agents and Chemotherapy, Mar. 1992 (pp. 626–631).

Article "Fatty Acids and Derivatives as Antimicrobial Agents" authored by Kabara (pp. 1–14).

Article "Production of Toxic Shock Syndrome Toxin 1 By Staphylococcus Aureus as Determined by Tampon Disk–Membrane–Agar Method" Authored by Robbins, Reisler, Hehl and Bergdoll, Journal of Clinical Microbiology, Aug. 1987 (pp. 1446–1449).

Aritcle "Toxic Shock Syndrome Staphlococcus Aureaus: Effect of Tampons on Toxic Shock Syndrome Toxin 1 Production" Authored by Schleivert, Blomster and Kelly (pp. 666–671).

Article "Fatty Acids Derivatives as Antimicrobial Agents" Authored by Kabara, Swieczkowski Conley and Truant. Antimicrobial Agents and Chemotherapy, Jul. 1972, pp. 23–28.

(List continued on next page.)

*Primary Examiner*—Jyothsna Venkat
*Attorney, Agent, or Firm*—Mark L. Davis

[57] ABSTRACT

Absorbent articles, such as catamenial tampons, for absorbing body fluids have included an effective amount of a nitrogen containing compound to substantially inhibit the production of exotoxins by Gram positive bacteria. The compound is one or more nitrogen containing compounds and their salts having the general formula:

$$R_1 - \underset{\underset{R_3}{|}}{N} - R_2$$

wherein $R_1$ is an alkyl group having from about 8 to about 18 carbon atoms; and $R_2$ and $R_3$ can be the same or different. $R_2$ and $R_3$ are selected from hydrogen and an alkyl group having from 1 to about 18 carbon atoms. The alkyl groups of $R_2$ and $R_3$ can have one or more substitutional moieties selected from hydroxyl, carboxyl and carboxyl salts, and imidazoline. A method of inhibiting the production of exoprotein from Gram positive bacteria is also disclosed.

9 Claims, No Drawings

OTHER PUBLICATIONS

Article "Magnesium, Staphylococcus Aureus and Toxic Shock Syndrome" Authored by Kaas Magnesium 1988:7:315–319.

"The Effect of Glycerol Monolaurate on Growth of, and Production of Toxic Shock Syndrome Toxin 1 and Lipase by Staphylococcus Aureus" Authored by Holland, Taylor and Farrell (pp. 41–55).

Article "Toxin and Enzyme Characterization of Staphylococcus Aureus Isolates From Patients With and Without Toxic Shock Syndrome" Authored by Schlievert et al. Annals of Internal Medicine, 1982:96 (Part 2):937–940.

"Detection and Quantitation of Toxic Shock Syndrome Toxin 1 in Vitro and In Vivo by Noncompetitive Enzyme–Linked Immunosorbent Assay" Authored by Rosten et al., Journal of Clinical Microbiology, Feb. 1987: pp. 327–332.

Article "Sequential Vaginal Cultures from Normal Young Women" Authored by Sautter et al. Journal of Clinical Microbiology, May 1980, pp. 479–484.

Article "Emerging Role of Lactobacilli in the Control and Maintenance of the Vaginal Bacterial Microflora" Authored by Redondo–Lopez et al., Reviews of Infectious Diseases—vol. 12, No. 5 pp. 856–872.

Article "Nasal and Vaginal Staphylococcus Aureus in Young Women: Quantitive Studies" Annals of Inernal Medicine, 1982:96 (Part 2):951–953.

Article "Methods for Quantitative and Qualitative Evaluation of Vaginal Microflora during Menstruation" Authored by Onderdonk, Zamarchi, Walsh, Mellor, Munoz and Kass, Applied and Environmental Microbiology, Feb. 1986, pp. 333–339.

Article "The Vaginal Ecosystem", American Journal of Obstetrics and Gynecology, vol. 165, No. 4, Part 2, Oct., 1991.

Article "Vaginal Flora in Health and Disease" Authored by Bryan Larsen, Clinical Obstetrics Gynecology, vol. 36, No. 1, Mar. 1993.

Article "Recovery of Staphylococcus Aureus from Multiple Body Sites in Menstruating Women" Authored by Lansdell et al. Journal of Clinical Microbiology, Sep. 1984 pp. 307–310.

Article "Control of the Microbial Flora of the Vagina by $H_2O_2$–Generating Lactobacilli" Authored By Klebanoff et al., Dept. of Medicine of Obstetrics and Gynecology, The Journal of Infectious Diseases 1991:164:94–100.

Article "Quantitative Bacteriology of the Vaginal Flora" Authored by Bartlett et al., The Journal of Infectious Diseases, vol. 136, No. 2.

INHIBITION OF EXOPROTEIN USING AMINE COMPOSITIONS IN ABSORBENT ARTICLE AND METHOD THEREOF

FIELD OF THE INVENTION

The present invention relates improvements in disposable absorbent devices, such as vaginal tampons and sanitary napkins. More particularly, the invention relates to the incorporation of amine compositions into such absorbent articles and these compounds effects on Gram positive bacteria.

BACKGROUND OF THE INVENTION

Disposable absorbent devices for the absorption of human exudates are widely used. These disposable devices typically have a compressed mass of absorbent formed into the desired shape, which is typically dictated by the intended consumer use. In the area of a menstrual tampon, the device is intended to be inserted in a body cavity for absorption of the body fluids generally discharged during a woman's menstrual period.

There exists in the female body a complex process which maintains the vagina and physiologically related areas in a healthy state. In a female between the age of menarche and menopause, the normal vagina provides an ecosystem for a variety of microorganisms. Bacteria are the predominant type of microorganism present in the vagina; most women harbor about $10^9$ bacteria per gram of vaginal exudate. The bacterial flora of the vagina is comprised of both aerobic and anaerobic bacteria. The more commonly isolated bacteria are Lactobacillus species, corynebacteria, *Gardnerella vaginalis*, Staphylococcus species, Peptococcus species, aerobic and anaerobic Streptococcal species, and Bacteroides species. Other microorganisms that have been isolated from the vagina on occasion include yeast (*Candida albicans*), protozoa (*Trichomonas vaginalis*), mycoplasma (*Mycoplasma hominis*), chlamydia (*Chlamydia trachomatis*), and viruses (*Herpes simplex*). These latter organisms are generally associated with vaginitis or venereal disease, although they may be present in low numbers without causing symptoms.

Physiological, social and idiosyncratic factors affect the quantity and species of bacteria present in the vagina. Physiological factors include age, days of the menstrual cycle, and pregnancy. For example, vaginal flora present in the vagina throughout the menstrual cycle can include lactobacilli, corynebacterium, ureaplasma, and mycoplasma. Social and idiosyncratic factors include method of birth control, sexual practices, systemic disease (e.g. diabetes), and medication.

Bacterial proteins and metabolic products produced in the vagina can affect other microorganisms and the human host. For example, the pH of the vagina between menstrual periods is mildly acidic having a pH ranging from about 3.8 to about 4.5. This pH range is generally considered the most favorable condition for the maintenance of normal flora. At that pH, the vagina normally harbors the numerous species of microorganisms in a balanced ecology, playing a beneficial role in providing protection and resistance to infection and makes the vagina inhospitable to some species of bacteria such as *Staphylococcus aureus* (*S. aureus*). The low pH is a consequence of the growth of lactobacilli and their production of acidic products. Microorganisms in the vagina can also produce antimicrobial compounds such as hydrogen peroxide and bactericides directed at other bacterial species. One example is the lactocins, bacteriocin-like products of lactobacilli directed against other species of lactobacilli.

Some microbial products may affect the human host. For example, *S. aureus* can produce and excrete into its environment a variety of exoproteins including enterotoxins, Toxic Shock Syndrome Toxin-1 (TSST-1), and enzymes such as protease and lipase.

*S. aureus* is found in the vagina of approximately 16% of healthy women of menstrual age. Approximately 25% of the *S. aureus* isolated from the vagina are capable of producing TSST-1. TSST-1 and some of the staphylococcal enterotoxins have been identified as causing Toxic Shock Syndrome (TSS) in humans.

Symptoms of TSS generally include fever, diarrhea, vomiting and a rash followed by a rapid drop in blood pressure. Systemic vital organ failure occurs in approximately 6% of those who contact the disease. *S. aureus* does not initiate TSS as a result of the invasion of the microorganism into the vaginal cavity. Instead as *S. aureus* grows and multiplies, it can produce Toxic Shock Syndrome Toxin 1 (TSST-1; synonyms: pyrogenic exotoxin C and enterotoxin F). Only after entering the bloodstream does the TSST-1 toxin act systemically and produce the symptoms attributed to Toxic Shock Syndrome.

Menstrual fluid generally has a pH of approximately 7.3. During menses the pH of the vagina moves toward neutral and can become slightly alkaline. This change permits microorganisms whose growth is inhibited by an acidic environment the opportunity to proliferate. For example, *S. aureus* is more frequently isolated from vaginal swabs during menstruation than from swabs collected between menstrual periods.

There have been numerous attempts to reduce or eliminate pathogenic microorganisms and menstrually occurring TSS by incorporating into a tampon pledget one or more biostatic, biocidal, and/or detoxifying compounds. For example, L-ascorbic acid has been applied to a menstrual tampon to detoxify toxin found in the vagina of the human female during menstruation.

Incorporating glyceryl triacetate into a tampon pledget has been suggested. Glyceryl triacetate is readily broken down into glycerol and acetic acid by the enzymatic action of esterase. Esterase is present in the vaginal epithelium and in menstrual fluid. The enzymatic action of the esterase is in turn controlled by the pH of the environment, being more active when the pH is on the alkaline side. Since the pH of the vagina moves toward the alkaline side during menstruation, the enzymatic activity of the esterase automatically increases and attacks the glyceryl triacetate. This releases acetic acid rapidly, which has the potential to reduce the pH and enzymatic activity of the esterase. However, menstrual fluid is well buffered and the acetic acid is ineffective at lowering the pH of the menstrual fluid.

Others have incorporated monoesters and diesters of polyhydric aliphatic alcohols and a fatty acid containing from 8 to 18 carbon atoms. For example, glycerol monolaurate (GML) has been used to inhibit the production of *S. aureus* enterotoxins and TSST-1. However, as noted above, esterase is abundantly present in the vaginal epithelium and menstrual fluid. This esterase, in combination with esterase and lipase produced by bacteria can enzymatically degrade the esters into non-effective compounds.

Until now, persons skilled in the art have not appreciated the affects of lipase and esterase on ester compounds. Thus, one or more ester compounds may have to be added to the absorbent article, such as a tampon pledget, in sufficiently high concentrations to detrimentally effect the normal flora present in the vaginal area. When the natural condition is altered, overgrowth by pathogen(s) may take place resulting in a condition known as vaginitis.

Accordingly, there exists a need for an absorbent product that has incorporated therein a compound that will: effectively inhibit the production of exoproteins, such as TSST-1 and Enterotoxin B, from Gram positive bacteria; and will be substantially unaffected by the enzymes lipase and esterase.

SUMMARY OF THE INVENTION

Briefly, the present invention is based on the discovery that when an effective amount of one or more nitrogen containing compounds are incorporated into an absorbent article, such as a catamenial tampon, the production of exoprotein from Gram positive bacterium is substantially inhibited. The nitrogen containing compounds of the invention can be represented by the general formula:

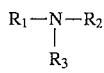

wherein $R_1$, is an alkyl group having from about 8 to about 18 carbon atoms; and $R_2$ and $R_3$ can be the same or different and are independently selected from hydrogen and alkyl group(s) having from 1 to about 18 carbon atoms. The alkyl groups of $R_2$ and $R_3$ can include one or more substitutional moieties selected from hydroxyl, carboxyl and carboxyl salts and imidazoline. It is also within the scope of this invention for the nitrogen containing compound to include an amine salt. The amine compound and salts thereof are effective in substantially inhibiting the production of exoprotein from Gram positive bacteria.

It is a general object of the invention to provide an absorbent article which inhibits the production of exoproteins from Gram positive bacterium. A more specific object of the invention is to provide a catamenial tampon incorporating one or more amine compounds which act to substantially inhibit the production of TSST-1 and Enterotoxin B by S. aureus.

Another object of the invention is to provide a catamenial tampon that has incorporated therewith one or more amine compounds that will substantially inhibit the production of exoproteins from Gram positive bacterium without significantly imbalancing the natural flora present in the vaginal tract.

Another object of the invention is to provide a method for inhibiting the production exoprotein produced by Gram positive bacteria in an absorbent article.

Other objects and advantages of the invention, and modifications thereof, will become apparent to persons skilled in the art without departure from the inventive concepts defined in the appended claims.

DETAILED DESCRIPTION OF THE INVENTION

The invention will be described in detail in connection with a catamenial tampon, but would be understood by persons skilled in the art to be applicable to other disposable absorbent articles such as sanitary napkins, panty liners, adult incontinent undergarments, diapers, medical bandages and tampons such as those intended for medical, dental, surgical, and/or nasal use wherein inhibition of exoproteins from Gram positive bacteria would be beneficial.

Vaginal tampons suitable for use in this invention are usually made of absorbent fibers, including natural and synthetic fibers, compressed into a unitary body of a size which may easily be inserted into the vaginal cavity. They are normally made in an elongated cylindrical form in order that they may have a sufficiently large body of material to provide the required absorbing capacity, but may be made in a variety of shapes. The tampon may or may not be compressed, although compressed types are now generally preferred. The tampon may be made of various fiber blends including both absorbent and nonabsorbent fibers, which may or may not have a suitable cover or wrapper.

It has been found that certain nitrogen containing compounds can substantially inhibit the production of exoprotein of Gram positive bacteria, and more specifically, the production of TSST-1 and Enterotoxin B from S. aureus bacterium. The nitrogen containing compounds of the invention are amines and their salts having the general formula:

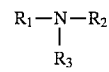

wherein $R_1$ is an alkyl group having from about 8 to about 18 carbon atoms; and $R_2$ and $R_3$ can be the same or different and are selected from hydrogen and alkyl group(s) having from 1 to about 18 carbon atoms. The $R_2$ and $R_3$ alkyl groups can include one or more substitutional moieties selected from hydroxyl, carboxyl and carboxyl salts and imidazoline. The amine compounds of the invention are effective in substantially inhibiting the production of exoprotein from Gram positive bacteria.

It is critical to the invention that the $R_1$ moiety be an alkyl group having from about 8 to about 18 carbon atoms. Desirably, the alkyl group is derived from fatty acid compounds which include, without limitation, caprylic, capric, lauric, myristic, palmitic and stearic acid whose carbon chain lengths are 8, 10, 12, 14, 16 and 18, respectively. Highly preferred materials include capric, lauric, and myristic. Preferred unsaturated fatty acids are those having one or two cis-type double bonds and mixtures of these materials. Suitable materials include myrystoleic, palmitoleic, linolenic and mixtures thereof.

The $R_2$ and $R_3$ alkyl groups can further include one or more substitutional moieties selected from hydroxyl, carboxyl, carboxyl salts, and $R_1$ and $R_2$ can form an unsaturated heterocyclic ring that contains a nitrogen that connects via a double bond to the alpha carbon of the $R_1$ moiety to form a substituted imidazoline. The carboxyl salts can have one or more cations selected from sodium, potassium or both. The $R_1$–$R_3$ alkyl groups can be straight or branched and can be saturated or unsaturated.

In another embodiment, the amine compound can be a salt. The salt can be represented by the general formula:

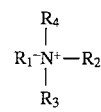

wherein $R_1$ is an anionic moiety associated with the amine and is derived from an alkyl group having from about 8 to about 18 carbon atoms. Desirably, $R_1$ is a polyalkyloxylated alkyl sulfate. The $R_4$ moiety is the same as that described above for the $R_2$ and $R_3$ moieties. The $R_1$–$R_4$ alkyl groups can be straight or branched and can be saturated or unsaturated. A preferred compound illustrative of an amine salt is TEA laureth sulfate.

Preferred amine compounds of the present invention which may be incorporated into the absorbent article or onto the cover thereof include: TEA laureth sulfate, lauramine, lauramino propionic acid, sodium lauriminodipropionic acid, lauryl hydroxyethyl imidazoline and mixtures thereof.

In accordance with the invention, the tampon contains an effective amount of the inhibiting nitrogen containing compound to substantially inhibit the formation of TSST-1 when the tampon is exposed to *S. aureus* bacteria. Effective amounts have been found to be at least about $1\times(10^{-5})$ millimoles of the amine compound per gram of absorbent. Preferably, the amine compound ranges from about 0.0005 millimoles per gram of absorbent to about 2 millimoles per gram of absorbent and more preferably 0.005 millimoles per gram of absorbent to about 0.2 millimoles per gram of absorbent. Although "compound" is used in the singular, one skilled in the art would understand that it includes the plural. That is, the absorbent article can include more than one amine compound.

The compositions of the present invention can be prepared and applied in any suitable form, but are preferably prepared in forms including, without limitation aqueous solutions, lotions, balms, gels, salves, ointments, boluses, suppositories, and the like.

The compositions may be applied to the absorbent article using conventional methods for applying an inhibitory agent to the desired absorbent article. For example, unitary tampons without separate wrappers may be dipped directly into a liquid bath having the agent and then can be air dried, if necessary to remove any volatile solvents. For compressed tampons, impregnating any of its elements is best done before compressing. The compositions when incorporated on and/or into the tampon materials may be fugitive, loosely adhered, bound, or any combination thereof. As used herein the term "fugitive" means that the composition is capable of migrating through the tampon materials.

It is not necessary to impregnate the entire absorbent body of the tampon with the inhibitory agent. Optimum results both economically and functionally, can be obtained by concentrating the material on or near the outer surface where it will be most effective during use.

The substantially inhibitory amine compositions may additionally employ one or more conventional pharmaceutically-acceptable and compatible carrier materials useful for the desired application. The carrier can be capable of co-dissolving or suspending the materials used in the composition. Carrier materials suitable for use in the instant composition, therefore, include those well-known for use in the cosmetic and medical arts as a basis for ointments, lotions, creams, salves, aerosols, suppositories, gels and the like.

The amine compositions of the present invention may additionally employ adjunct components conventionally found in pharmaceutical compositions in their art-established fashion and at their art-established levels. For example, the compositions may contain additional compatible pharmaceutically active materials for combination therapy, such as supplementary antimicrobials, anti-parasitic agents, antipruritics, astringents, local anaesthetics, or anti-inflammatory agents.

The invention may be readily understood by considering the following examples illustrative of specific embodiments of the invention.

EXAMPLE A

The efficacy of the test compounds on TSST-1 production was determined by placing the desired concentration, expressed in millimoles/milliliter (millimolar hereinafter mM) of the active compound in 10 milliliters of a Growth Medium of each test compound in a Corning 50 ml conical polystyrene tube. The polystyrene tube is available from Scientific Products Division, Baxter Diagnostics Incorporated, 1430 Waukegan Road, McGaw Park, Ill. 60085-6787.

The Growth Medium was prepared as follows: Brain heart infusion broth (BHI), available from Becton Dickinson Microbiology Systems, Cockeysville, Md. 21030, was dissolved and sterilized according to the manufacturer's instructions. Ninety milliliters of BHI broth was supplemented with 10 ml fetal bovine serum (FBS), available from Sigma Chemical Company, P.O. Box 14508, St. Louis, Mo. 63178-9916. One milliliter of a 0.02 molar sterile solution of the hexahydrate of magnesium chloride, available from Sigma Chemical Company, was added to the BHI-FBS mixture. One milliliter of a 0.027 molar sterile solution of L-glutamine available from Sigma Chemical Company was also added to the BHI-FBS mixture.

If the test compound was not water soluble or water miscible, it was first dissolved at 50 times the desired concentration in 10 ml isopropanol, then diluted to the desired final concentration in 10 ml of the Growth Medium. Tubes of Growth Medium with an equivalent amount of isopropanol, but no test compound, were prepared as controls.

In preparation for inoculation of the tubes of Growth Medium containing the test compound, an inoculating broth was prepared as follows. *S. aureus*, (MN8) was streaked onto a sheep blood agar plate and incubated at 37° C. The test organism in this Example was obtained from Dr. Pat Schlievert, Department of Microbiology of the University of Minnesota Medical School, Minneapolis, Minn. After 24 hours of incubation three to five individual colonies were picked with a sterile inoculating loop and used to inoculate 10 ml of the Growth Medium. The tube of inoculated Growth Medium was capped with a S/P® diSPo® plug available from Scientific Products Division, Baxter Diagnostics, Incorporated and incubated at 37° C. in atmospheric air having 5% by volume $CO_2$. After 24 hours of incubation, the culture was removed from the incubator and mixed well on a S/P brand vortex mixer. A second tube containing 10 ml of the Growth Medium was inoculated with 0.5 ml of the above 24 hour culture and re-incubated at 37° C. in atmospheric air having 5% by volume $CO_2$. After 24 hours of incubation the culture was removed from the incubator and mixed well on a S/P brand vortex mixer. Each tube of Growth Medium containing a test compound and growth control tubes with or without isopropanol were inoculated with 0.1 ml of the prepared inoculating broth. The initial colony forming units (CFU) per ml of Growth Medium were approximately $1\times10^7$. The tubes were capped with S/P® diSPo® plugs and incubated at 37° C. in atmospheric air having 5% by volume $CO_2$. After 24 hours of incubation the tubes were removed from the incubator and the culture fluid was assayed for the number of colony forming units of *S. aureus* and prepared for analysis of TSST-1 per method described below.

The number of colony forming units per ml after incubation was determined by standard plate count procedure. The culture fluid broth was centrifuged and the supernatant subsequently filter sterilized through an Acrodisc® syringe filter unit available from Scientific Products Division, Baxter Diagnostics, Inc. The resulting fluid was frozen at −80° C. until assayed.

The amount of TSST-1 per milliliter was determined by a non-competitive, sandwich enzyme-linked immunoabsorbent assay (ELISA). Samples of the culture fluid and the TSST-1 reference standard were assayed in triplicate. The method employed was as follows: Four reagents, rabbit polyclonal anti-TSST-1 IgG (#LTI-101), rabbit polyclonal anti-TSST-1 IgG conjugated to horseradish peroxidase (#LTC-101), TSST-1 (#TT-606), and normal rabbit serum certified anti-TSST-1 free (#NRS-10) were purchased from Toxin Technology, Incorporated, 7165 Curtiss Avenue, Sarasota, Fla., 34231. Sixty-two microliters of polyclonal rabbit anti-TSST-1 IgG (#LTI-101) was appropriately diluted so that a 1:100 dilution gave an absorbance of 0.4 at 650 nanometers. This was added to 6.5 ml of 0.5 molar carbonate buffer, pH 9.6, and 100 microliters of this solution was pipetted into the inner wells of polystyrene microtiter plates #439454, obtained from Nunc-Denmark. The plates were covered and incubated overnight at 37° C. Unbound antitoxin was removed by three washes with phosphate buffered saline (pH 7.2)(0.011 molar $NaH_2PO_4$ and 0.9% [wt/vol] NaCl both available from Sigma Chemical Company) containing 0.5% [vol/vol] Tween 20 (PBS-Tween), also available from Sigma Chemical Company. The plates were treated with 100 microliters of a 1% [wt/vol] solution of bovine serum albumin (BSA), available from Sigma Chemical Company, covered, and incubated at 37° C. for one hour. Unbound BSA was removed by 6 washes with PBS-Tween. TSST-1 reference standard, serially diluted from 1–10 ng/ml in PBS-Tween, test samples treated with normal rabbit serum 10% [vol/vol] final concentration and reagent controls were pipetted in 100 microliter volumes to their respective wells. This was followed by incubation for two hours at 37° C. and three washes to remove unbound toxin. The rabbit polyclonal anti-TSST-1 IgG conjugated to horseradish peroxidase and diluted according to manufacturer's instructions was added (100 microliter volumes) to each microtiter well. The plates were covered and incubated at 37° C. for one hour.

Following incubation the plates were washed 6 times in PBS-Tween. Following this, the wells were treated with a solution consisting of 0.075 molar sodium citrate (pH 4.0), 0.6 millimolar 2,2'-Azino-bis-(3-ethylbenzthiazoline-6-sulfonic acid) diammonium salt and 0.009% [vol/vol] hydrogen peroxide, all available from Sigma Chemical Company. The intensity of the color reaction in each well was evaluated over time using a BioTek Model EL340 Microplate reader (OD 405 nm) and Kineticalc® software available from Biotek Instruments, Inc. TSST-1 concentrations in test samples were predicted from the reference toxin regression equations derived during each assay procedure. The efficacy of the compound in inhibiting the production of TSST-1 is shown in Table I below.

TABLE I

| Compound | mM Test Compound | CFU/ml | ELISA: TSST-1 ng/ml |
|---|---|---|---|
| Growth Control | None | $2.5 \times 10^9$ | 153.2 |
| Laurimino propionic acid | 10.67 | No Growth | <1.1 |
|  | 0.43 | Not Determined* | 24.2 |
| Sodium lauriminodipropionic acid | 10.67 | $1.0 \times 10^3$ | <1.1 |
|  | 2.15 | Not Determined | 2.9 |
| Lauryl hydroxyethyl imidazoline | 10.67 | No Growth | <1.1 |
|  | 0.43 | Not Determined | 85.9 |
| TEA laureth sulfate | 10.67 | $6.2 \times 10^2$ | <1.1 |
|  | 2.15 | None Detected | 4.7 |
| Lauramine | 10.67 | No Growth | <1.1 |
|  | 2.15 | Not Determined | 77.0 |

*S. aureus grew in the culture broth, the amount of growth was not determined.
The above list of compounds (Commercial Name), their percent active compound, and vendor are as follows:
Laurimino propionic acid, (Mackam 151L), 40%, McIntyre Group, LTD, 1000 Governors Highway, University Park, IL. 60466.
Sodium lauriminodipropionic acid, (Deriphat 160-C.), 30%, Henkle/Cospha, Cospha Group, 300 Brookside Ave., Ambler, PA 19002.
Lauryl hydroxyethyl imidazoline, (Schercozoline L), Scher Chemicals, Inc., Industrial West, P.O. Box 4317, Clifton, NJ 07012.
TEA laureth sulfate, (Sulfochem TLES), 39%, Chemron, P O Box 2299, Paso-Robles, CA 93447.
Lauramine,(Dodecylamine), 99+, Aldrich, 1001 West Saint Paul Ave, Milwaukee, WI 53233.

In accordance with the present invention, the data in Table 1 shows that S. aureus MN8, when compared to the control, produced significantly less TSST-1 in the presence of the amine compounds. The amine compounds reduced the amount of exotoxin production ranging from about 86 percent to greater than 99.4 percent.

EXAMPLE B

The efficacy of the test compounds in reducing the production of a second exoprotein of S. aureus was determined using S. aureus HOCH, a known producer of Enterotoxin B. The test organism in this Example was obtained from Dr. Pat Schlievert, Department of Microbiology of the University of Minnesota Medical School, Minneapolis, Minn. The experimental procedure for assessing the efficacy of the test compounds effect on growth of S. aureus HOCH and for production of a culture filtrate was the same as set forth in Example A above.

The amount of S. aureus enterotoxin B per milliliter was determined by Western Blot assay. Samples of the culture fluid and the Staphylococcal Enterotoxin B (SEB) reference standard were assayed in triplicate. The method employed was similar to that described in "A Rapid, Sensitive Method for Detection of Alkaline Phosphatase-Conjugated Anti-Antibody on Western Blots," M. S. Blake, K. H. Johnston, G. J. Russell-Jones and E. C. Gotschlich, *Analytical Biochemistry*, 136: 175–179, 1984. The disclosure of which is incorporated herein by reference. Enterotoxin B was separated from other proteins in the test samples by sodium dodecyl sulfate-polyacrylamide gel (SDS-PAGE) electrophoresis. The upper stacking gel used 3% acrylamide gel, the lower separating gel contained 14% acrylamide gel. The upper gel was prepared with a comb containing twenty lanes spanning 15.5 centimeters of the top of the stacking gel. A low molecular weight SDS-PAGE standard, BioRad #161-0305 available from Bio-Rad Laboratories having offices at 2000 Alfred Nobel Drive, Hercules, Calif. 94547, SEB, #BT-202 from Toxin Technology, Incorporated, and culture extracts, as prepared above, were each mixed 1:1 with a loading buffer. The loading buffer contained 30% [vol/vol] glycerol, 15% [vol/vol] mercaptoethanol, 7% [wt/vol] sodium dodecyl sulfate, 0.0036% [wt/vol] bromphenol blue, and 0.76% [wt/vol] Trizma base with a pH of 6.8. The mixtures were boiled for 5 minutes, then twenty-five (25) microliters of each mixture was placed in a lane. The SDS-PAGE gel was electrophoresed (60 to 80 volts) for 90 minutes or until the dye front was through the stacking gel and for an additional 2.5 hours (160–170 volts) with an electrophoresis buffer of 0.61% [wt/vol]Tris base, 2.85% [wt/vol] glycine, 0.1% [wt/vol] SDS, pH 7.85. Proteins were transferred to a nitrocellulose transfer membrane, available from Schleicher and Schull, Inc., Keene, N.H. 03431, #BA 85, overnight approximately 15 hours at 200 milliamps in a Bio-Rad Trans-Blot® cell. The transfer buffer was composed of 0.3% [wt/vol] Tris base, 1.4% [wt/vol] glycine, 20% [vol/vol] methanol, pH 7.6.

The nitrocellulose membrane was treated for 45 minutes at 37° C. with 3% [wt/vol] gelatin in 0.02 molar Tris buffer, 0.5 molar NaCl, at pH 7.5 (TBS) to block non-specific reactions, then washed at 37° C. with TBS-0.05% [vol/vol] Tween 20 (TBS-Tween) for 45 minutes. The membrane was then submerged for 1.5 hours at 37° C. in 50 ml TBS-Tween containing 0.05 ml rabbit polyclonal anti-SEB IgG, #LBI-202 available from Toxin Technology, Incorporated.

The membrane was washed two times in TBS-Tween, then submerged a second time for 1.5 hours at 37° C. in a 50 ml solution of TBS-Tween with 25 microliters of goat anti-rabbit IgG conjugated to alkaline phosphatase. The membrane was washed twice in TBS-Tween and twice in TBS. The blot was developed with a reaction solution consisting of 2 mg 5-bromo-4-chloroindolyl phosphatase, 100 microliters of N,N dimethyl formamide, 18 ml 0.15 molar barbitol buffer, pH 9.2, 2 mg nitroblue tetrazolium, and 40 microliters of a 2 molar solution of $MgCl_2$ $6H_2O$, all available from Sigma. The reaction was stopped with a cold water wash. The amount of SEB produced in the presence of the test compound was estimated by a comparison with the staining intensity produced by a serial dilution of SEB. The efficacy of the test compound in inhibiting the production of Enterotoxin B is shown in Table II below.

TABLE II

| Compound | mM Test Compound | CFU/ml | Western Blot: SEB mg/ml |
|---|---|---|---|
| Growth control | None | $7.0 \times 10^9$ | 0.8 |
| Laurimino | 10.67 | No growth | None detected |
| Propionic acid | 0.43 | Not determined* | None detected |
| Sodium lauriminodipropionic acid | 10.67 | $1.3 \times 10^3$ | None detected |
| | 2.15 | Not determined | None detected |
| Lauryl hydroxyethyl imidazoline | 10.67 | No growth | None detected |
| | 0.43 | Not determined | None detected |
| TEA laureth sulfate | 10.67 | $5.6 \times 10^2$ | None detected |
| | 2.15 | Not determined | None detected |
| Lauramine | 10.67 | No growth | None Detected |
| | 2.15 | Not determined | 0.2 |

*S. aureus grew in the culture broth, the amount of growth was not determined.

In accordance with the present invention, the data in Table II shows that *S. aureus* HOCH produced significantly less SEB in the presence of the amine compounds. Compared to the control, the amine compounds reduced the amount of exotoxin production below the detectable range of 0.16 milligrams/milliliter.

Another aspect of the invention is for a method of inhibiting the production of exoprotein from Gram positive bacteria in an absorbent product. In the method, the absorbent article, such as a tampon, is contacted with one or more of the above described amine and/or amine salt compositions. The absorbent article has absorbed or coated on the fibers or cover material an effective amount of the amine composition so that the production of exoprotein from Gram positive bacteria contacting the absorbent product is inhibited. Desirably, the production of TSST-1 and Enterotoxin B are inhibited.

The above description and Examples are given to serve as a guide in carrying out the invention and are not to be construed as a limitation or limitations of the invention. It will be understood that various changes or modifications may be made, as will be apparent to those skilled in the art, without departing from the spirit of the invention or the scope of the claims annexed hereto.

I claim:

1. An absorbent article comprising an effective amount of an amine compound having the formula;

$$R_1-\underset{\underset{R_3}{|}}{N}-R_2$$

wherein $R_1$ is alkyl group having from 8 to 18 carbon atoms; and $R_2$ and $R_3$ can be the same or different and are selected from the group consisting of hydrogen and alkyl group having from 1 to 18 carbon atoms and which can have one or more substitutional moieties selected from the group consisting of hydroxyl, carboxyl, carboxyl salts, and imidazoline wherein said compound is effective in substantially inhibiting the production of exoprotein from Gram positive bacteria.

2. The absorbent article of claim 1 wherein said carboxyl salt has a cationic moiety selected from the group consisting of sodium, potassium and combinations thereof.

3. The absorbent article of claim 1 wherein said amine compound is selected from the group consisting of lauramine, lauramino propionic acid, sodium lauriminodipropionic acid, lauryl hydroxyethyl imidazoline and mixtures thereof.

4. The absorbent article of claim 1 wherein said amine compound is present in an amount greater than about $1\times(10^{-5})$ millimoles per gram of absorbent.

5. The absorbent article of claim 1 wherein said amine compound is present in an amount ranging from about 0.0005 millimoles per gram of absorbent to about 2 millimoles per gram of absorbent.

6. An absorbent article comprising an effective amount of an amine salt having the formula:

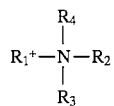

wherein $R_1^+$ is alkyl group having from 8 to 18 carbon atoms; and $R_2$–$R_4$ can be the same or different and are selected from the group consisting of hydrogen and alkyl group having from 1 to 18 carbon atoms and which can have one or more substitutional moieties selected from the group consisting of hydroxyl, carboxyl, carboxyl salts, and imidazoline wherein said compound is effective in substantially inhibiting the production of exoprotein from Gram positive bacteria.

7. A method of inhibiting the production of exoprotein from Gram positive bacteria in an absorbent product comprising the steps of contacting said absorbent product with an effective amount of an amine compound wherein said amine compound is selected from the group consisting of lauramine, lauramino propionic acid, sodium lauriminodipropionic acid, lauryl hydroxyethyl imidazoline and mixtures thereof, said amine compound being present in an amount greater than about $5\times(10^{-4})$ millimoles per gram of absorbent in said absorbent product and exposing said absorbent product to at least one Gram positive bacteria.

8. The method of claim 7 wherein said Gram positive bacteria is TSST-1 producing *Staphylococcus aureus* bacteria.

9. The method of claim 7 wherein said Gram positive bacteria is Enterotoxin B producing *Staphylococcus aureus* bacteria.

* * * * *